United States Patent
Mysliwiec

[19]

[11] Patent Number: 5,826,475
[45] Date of Patent: Oct. 27, 1998

[54] KNIFE SHAFT ASSEMBLY

[75] Inventor: Stefan Alojzy Mysliwiec, Kaukauna, Wis.

[73] Assignee: Kimberly-Clark Worldwide, Inc., Neenah, Wis.

[21] Appl. No.: 928,892

[22] Filed: Sep. 12, 1997

Related U.S. Application Data

[63] Continuation of Ser. No. 667,579, Jun. 21, 1996, abandoned.

[60] Provisional application No. 60/010,636, Jan. 26, 1996.

[51] Int. Cl.$^6$ .................................. B26D 7/18; B26F 1/38
[52] U.S. Cl. .................................. 83/116; 83/346; 83/669
[58] Field of Search .............................. 53/113, 115, 116, 53/117, 118, 346, 663, 669

[56] References Cited

U.S. PATENT DOCUMENTS

| | | | |
|---|---|---|---|
| 1,044,931 | 11/1912 | Simmons | 83/669 |
| 1,363,526 | 12/1920 | Malm . | |
| 2,113,843 | 4/1938 | Kavle | 83/117 |
| 2,145,048 | 1/1939 | Hagen . | |
| 2,525,987 | 10/1950 | Williamson | 83/117 |
| 3,488,778 | 1/1970 | Goujon et al. | 2/224 |
| 3,508,458 | 4/1970 | Cunningham | 83/346 X |
| 3,526,163 | 9/1970 | Lowery | 83/116 X |
| 3,552,244 | 1/1971 | Smith, Jr. | 83/116 X |
| 3,663,962 | 5/1972 | Burger | 2/224 |
| 3,744,384 | 7/1973 | Jarritt et al. . | |
| 3,881,490 | 5/1975 | Whitehead et al. | 128/287 |
| 4,289,166 | 9/1981 | Haines | 137/846 |
| 4,499,802 | 2/1985 | Simpson | 83/117 |
| 4,589,876 | 5/1986 | Van Tilburg | 604/385 R |
| 4,670,960 | 6/1987 | Provost | 29/415 |
| 4,862,574 | 9/1989 | Seidy | 29/415 |
| 5,048,589 | 9/1991 | Cook et al. | 162/109 |
| 5,111,725 | 5/1992 | Simpson et al. | 83/117 |
| 5,399,412 | 3/1995 | Sudall et al. | 428/153 |
| 5,452,634 | 9/1995 | Wilson | 83/346 X |

FOREIGN PATENT DOCUMENTS

| | | |
|---|---|---|
| 546 829 | 4/1956 | Belgium . |
| 0 391 299 A3 | 10/1990 | European Pat. Off. . |
| 06 70153A1 | 9/1995 | European Pat. Off. . |
| 1572994 | 7/1969 | France . |
| 1 442 308 | 7/1976 | United Kingdom . |
| 2 024 081 | 1/1980 | United Kingdom . |
| WO 92/19451 A1 | 11/1992 | WIPO . |

*Primary Examiner*—Eugenia A. Jones
*Attorney, Agent, or Firm*—Thomas J. Connelly; Douglas G. Glantz

[57] ABSTRACT

A knife shaft assembly is disclosed for use in a rotary die cutter. The knife shaft assembly includes a rotatable die shaft having an outer circumference and having a defined width. At least two die cutting inserts are mounted on the outer circumference of the die shaft. Each of the inserts has a first surface and a knife formed about the periphery of the first surface. The knife shaft assembly also includes a compressible material positioned between the die cutting inserts which prevent the buildup of material waste there between.

20 Claims, 3 Drawing Sheets

KNIFE SHAFT ASSEMBLY

This application is a continuation of application Ser. No. 08/667,579 entitled "A KNIFE SHAFT ASSEMBLY" and filed in the U.S. Patent and Trademark Office on Jun. 21, 1996, now abandoned.

FIELD OF THE INVENTION

This application claims priority from U.S. Provisional application Ser. No. 60/010,636 filed on Jan. 26, 1996. This invention relates to a knife shaft assembly for a rotary die cutter. More specifically, this invention relates to a knife shaft assembly with die cutting inserts and means for preventing a buildup of material waste between adjacent inserts.

BACKGROUND OF THE INVENTION

A rotary die cutter includes a rotatable anvil roll which cooperates with a rotatable knife shaft assembly. The knife shaft assembly has an outer circumference with two or more die cutters mounted thereon. The knife shaft assembly cooperates with the anvil roll to form a nip through which a web of material can pass. As the web of material passes between the nip, the die cutter will cut the material into a predetermined shape.

It is common practice to form the knife shaft assembly from a single die shaft by machining the cutting edges into the outer circumference thereof. By doing so, one can control to very close tolerances the outside diameter of the knife shaft assembly and therefore maintain a predetermined dimension between the nip. However, it is very expensive to machine the knife shaft assembly from a single metal piece. It is much more advantageous to machine individual die cutting inserts and then mount the inserts onto the outer circumference of a die shaft. Doing so substantially reduces the cost of producing the knife shaft assembly. However, the use of replaceable die cutting inserts present two challenges. First, up until now, when an insert was interchanged with another insert, it was necessary to regrind all of the knife edges of all of the inserts mounted on the circumference of the die shaft in order to assure that the nip dimension would not change. A second challenge with the use of replaceable die cutting inserts is that cut waste material could build up between the adjacent cutting edges. A buildup of such waste would reduce the ability of the knife shaft assembly to completely cut through the web passing through the nip.

Now, a knife shaft assembly has been invented which utilizes a compressible material between adjacent cutting edges of the inserts to prevent the build-up of waste material.

SUMMARY OF THE INVENTION

Briefly, this invention relates to a knife shaft assembly for a rotary die cutter. The knife shaft assembly includes a rotatable die shaft having an outer circumference and having a defined width. At least two die cutting inserts, preferably replaceable and/or interchangeable die cutting inserts, are mounted on the outer circumference of the die shaft. Each of the inserts has a first surface and a knife formed about the periphery of the first surface. The knife shaft assembly also includes a compressible material positioned between each pair of adjacent die cutting inserts which prevent the buildup of waste material.

The general object of this invention is to provide a knife shaft assembly with at least two die cutting inserts and means for preventing a buildup of waste material between the inserts. A more specific object of this invention is to provide a knife shaft assembly with replaceable and/or interchangeable die cutting inserts and a grid work of a compressible material located between the inserts for preventing the accumulation of cut waste material.

Another object of this invention is to provide a knife shaft assembly with a plurality of die cutting inserts and means for preventing a buildup of waste material so as to improve the die life.

A further object of this invention is to provide a knife shaft assembly with replaceable and/or interchangeable die cutting inserts utilizing multiple pieces of a compressible material to reduce waste material.

Still another object of this invention is to provide a knife shaft assembly with replaceable and/or interchangeable die cutting inserts utilizing compressible material between adjacent inserts to improve the efficiency of cutting various materials.

Still further, an object of this invention is to provide a knife shaft assembly with replaceable and/or interchangeable die cutting inserts utilizing a grid work of compressible material to reduce the initial cost to building a knife shaft assembly.

Other objects and advantages of the present invention will become more apparent to those skilled in the art in view of the following description and the accompanying drawings.

DETAILED DESCRIPTION OF THE PREFERRED EMBODIMENTS

Figure 1:
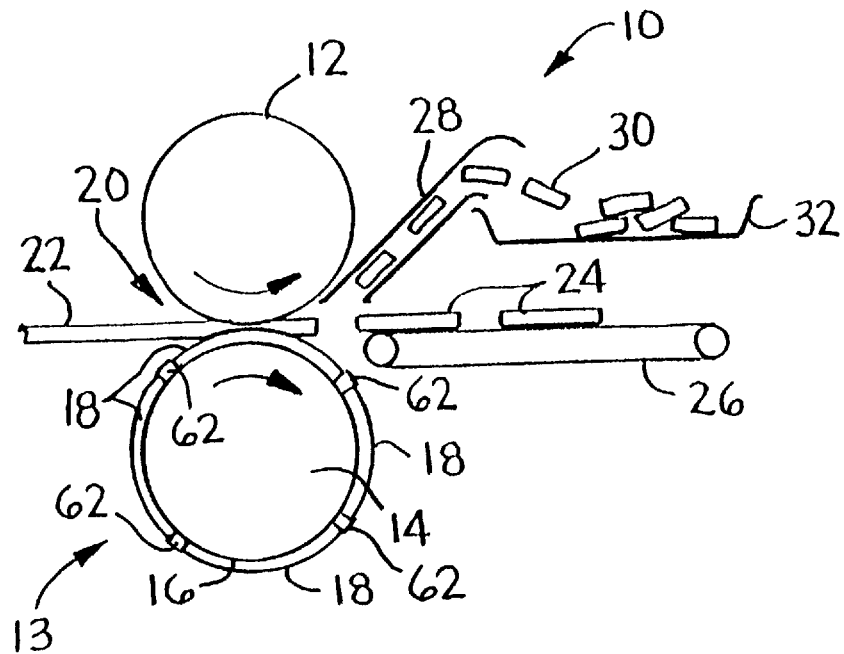
FIG. 1 is a schematic of a rotary die cutter showing a rotatable anvil roll cooperating with a rotatable knife shaft assembly to form a nip therebetween and having a web of material passing through the nip.

Referring to FIG. 1, a rotary die cutter 10 is shown which includes a rotatable anvil roll 12 cooperating with a rotatable knife shaft assembly 13. The anvil roll 12 can be constructed of a ferrous or non-ferrous metal and should have a smooth surface. The anvil roll 12 can be formed from a material which is compressible, such as natural or neoprene rubber or from a non-compressible material, such as steel. For most applications, it is preferred that the anvil roll 12 be a metal roll.

Figure 3:
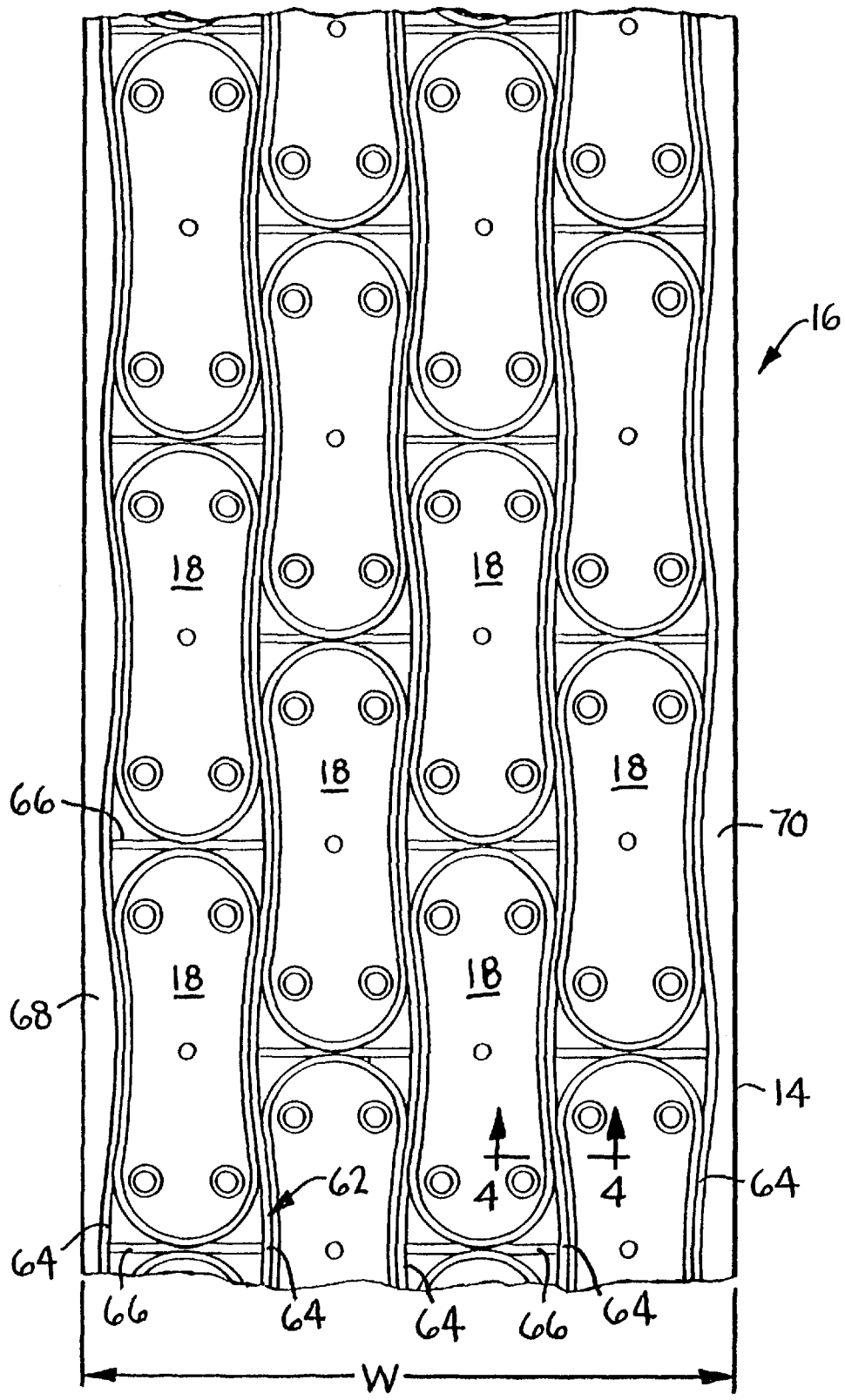
FIG. 3 is a top view of the circumference of a die shaft extended in planar form depicting the arrangement of the replaceable and/or interchangeable die cutting inserts and the compressible material positioned therebetween.

The knife shaft assembly 13 includes a rotatable die shaft 14 having an outer circumference 16 and a defined width "w," see FIG. 3. The die shaft 14 should be constructed out of a metal material, such as steel, and can vary in diameter to meet one's particular needs. The die shaft 14 can also vary in diameter. For most rotary die cutting applications, the diameter of the die shaft 14 can be between about 2 inches to about 12 inches. Larger diameters can be used if required. The die shaft 14 can have two or more inserts 18 mounted around its outer circumference 16. The exact number of inserts 18 which are utilized will depend upon a number of factors, including the size of each insert 18, the circumferential area and width of the die shaft 14, and the actual arrangement of the inserts 18 about the circumference of the die shaft 14, etc. For cutting articles, such as sanitary napkins and pantiliners, out of a web of absorbent material, the die shaft 14 can be constructed to have a diameter of between about 6 inches to about 18 inches, preferably, between about 6 inches to about 12 inches. The actual number of inserts 18 which can be mounted to the die shaft 14 can range from between about 2 to about 100, preferably between about 16 to about 52, and most preferably, between about 16 to about 24.

It should be noted that the efficiency of the knife shaft assembly 13 will increase when a plurality of die cutting inserts 18 are mounted onto the outer circumference 16 of the die shaft 14. As shown in FIG. 1, there are four die cutting inserts 18 mounted in a spaced apart configuration about the outer circumference 16 of the die shaft 14. Each of the inserts 18 has a central longitudinal axis X—X and a central transverse axis Y—Y. The inserts 18 can be arranged about the outer circumference 16 of the die shaft 14, such that each longitudinal axis X—X extends around at least a portion of the outer circumference 16 of the die shaft 14.

The anvil roll 12 and the knife shaft assembly 13 cooperate to form a nip 20 therebetween through which a web of material 22 can pass. As the anvil roll 12 and the knife shaft assembly 13 are rotated in opposite directions, the web of material 22 can pass through the nip 20 and be cut by the die cutting inserts 18 into individual articles 24. The articles 24 can be transported by conventional means, such as a conveyor 26, to a location where they can be stacked, packaged and later shipped. Any design waste, also referred to as "waste trim" 30 from the rotary die cutter 10 can be directed away from the nip 20 by a conduit 28 using vacuum, air pressure, gravity or mechanical means. The waste trim 30 can then be collected in a hopper 32 for possible recycling or some other means of disposal.

Figure 2:
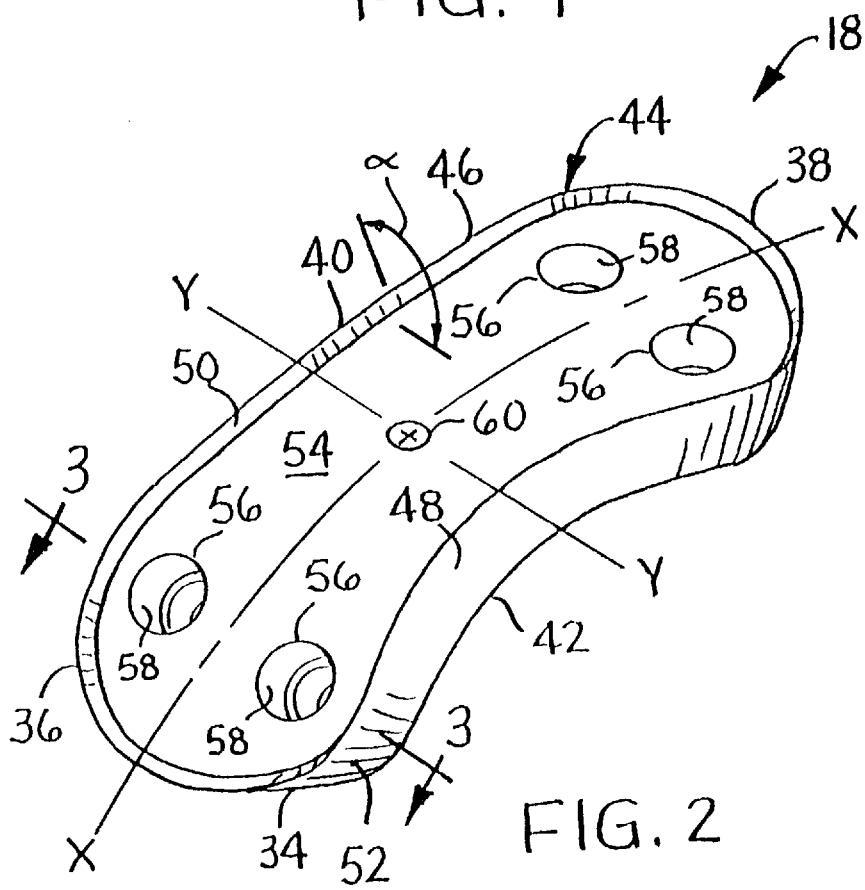
FIG. 2 is a perspective view of a replaceable and/or interchangeable die cutting insert.

Referring to FIG. 2, a die cutting insert 18 is shown before it is secured to the die shaft 14. The die cutting insert 18 can be a replaceable and/or interchangeable insert. By replaceable, it is meant that the insert 18 can be unbolted and removed from the die shaft 14 to be cleaned, reground or machined in some fashion and then bolted back onto the die shaft 14 in its original location. By interchangeable, it is meant that each of the die cutting inserts 18 is capable of being mutually interchanged with any other of the die cutting inserts 18. This interchangeability feature is very important because, up until now, it has been virtually impossible to produce replaceable and/or interchangeable inserts for a rotary die cutter 10 while still maintaining the nip dimension between the anvil roll 12 and the knife haft assembly 13.

The die cutting insert 18 has a base 34 formed on a predetermined radius. The base 34, which can have an arcuately-shaped profile, has first and second spaced apart ends, 36 and 38 respectively, and first and second oppositely aligned surfaces, 40 and 42 respectively. The first surface 40 will face the anvil roll 12 when the inserts 18 are assembled onto the knife shaft assembly 13. The second surface 42 will be concave so as to match the outer circumference 16 of the die shaft 14 onto which the insert 18 is to be secured. It is common to machine the second surface 42 to have a tolerance of plus or minus 0.0001 inches so as to facilitate a proper attachment between each of the die cutting insert 18 and the die shaft 14. If the second surface is not machined to a close tolerance to match the outer circumference 16 of the die shaft 14, then it is possible for additional compressive forces to develop as each insert 18 is secured to the die shaft 14. The presence of such compressive forces can alter the dimension of the nip 20, and this is undesirable.

As shown in FIG. 2, the die cutting insert 18 has a knife 44 which is integrally formed about the periphery of the first surface 40. Preferably, the knife 44 is a continuous element but could be serrated if desired. The knife 44 has a cutting edge 46 and first and second side walls, 48 and 50 respectively. The cutting edge 46 has a width of less than about 0.005 inches. Preferably, the width of the cutting edge 46 is between about 0.0005 to about 0.004 inches, and most preferably, the width is between about 0.001 to about 0.002 inches. The width of the cutting edge 46 is very important because if the width becomes too great, it will be more difficult to cleanly cut the material 22 passing through the nip 20. For example, instead of making a clean cut, the cutting edge 46 could compress the material 22 and allow the material 22 to be torn or broken and thereby produce a ragged cut.

The first side wall 48 is aligned approximately perpendicular to the cutting edge 46. In other words, the first side wall 48 is coextensively aligned with the outside periphery 52 of the base 34. Preferably, the first side wall 48 is aligned perpendicular, that is at 90 degrees, to the cutting edge 46. The second side wall 50 is aligned at an angle of at least about 15 degrees relative to the cutting edge 46. The second side wall 50 is located inward of the first side wall 48 and terminates at a third surface 54. The third surface 54 is located intermediate the first surface 40 and the second surface 42. The third surface 54 is spaced below the first surface by a relatively small distance. The actual distance between the first surface 40 and the third surface 54 can vary but normally will be about equal to the thickness of the article which is to be cut. For example, when cutting a compressible article having a total thickness of about 0.125 inches, the distance of the third surface 54 below the first surface 40 can be between about 0.1 inches to about 0.125 inches. This distance is equivalent to the height of the knife 44. The height of the knife 44 can be affected by the type of material 22 which is being cut, the thickness of the material, whether the material is compressible, whether the material is formed from a single layer or from a plurality of layers, whether the layers are bonded together by an adhesive, as well as the particular characteristics of the material itself. For example, a thermoplastic film may react differently to being cut than a fibrous nonwoven web. It should also be noted that when cutting thinner materials, the height of the knife 44 could be less than the thickness of the material 22 because the cut may not have to extend as far through the material as with a thicker product. When cutting the material 22, it is not necessary that the cutting edge 46 actually contact the anvil roll 12. In fact, the life of the cutting die insert 18 can be extended when the cutting edge 46 does not physically contact the anvil roll 12.

The second side wall 50 is aligned at an angle of at least about 15° relative to the cutting edge 46. Preferably, the angle is between about 15° to about 50° relative to the cutting edge 46, and more preferably, the angle is between about 15° to about 40° relative to the cutting edge 46. It is important that the second side wall 50 be angled relative to the cutting edge 46 at an angle of at least about 15° because the design of the insert 18 leaves very little support for the knife 44. Since the first side wall 48 is approximately perpendicularly aligned to the cutting edge 46, all support provided to the knife 44 will have to come from the material present between the first side wall 48 and the second side wall 50. If the angle is less than about 15°, there is a high probability that the cutting edge 46 will crack or chip as the material 22 is being cut because the forces acting on the cutting edge 46 can become very high.

As mentioned above, the die cutting insert 18 can be replaceable and/or interchangeable onto the die shaft 14. One means for removeably attaching the die cutting insert 18 to the die shaft 14 includes forming at least one aperture 56 adjacent to each of the first and second ends, 36 and 38 respectively. Preferably, a pair of apertures 56 are formed adjacent to each of the ends, 36 and 38 respectively, so as to permit each insert 18 to be correctly secured to the die shaft 14 without introducing unwanted forces into each insert 18. Each of the apertures 56 extends completely through the base 34 from the third surface 54 to the second surface 42. The apertures 56 are not threaded but do contain a counterbore 58 located adjacent to the third surface 54. Each counterbore 58 is sized and configured to receive the head of a machine bolt which can be used to attach the insert to the die shaft 14.

Each of the die cutting inserts 18 can also contain a pin hole 60 formed at the intersection of the central longitudinal axis X—X and the central transverse axis Y—Y. The pin hole 60 is designed to be coaxially aligned with a hole or bore formed in the die shaft 14 such that a pin (not shown) can be inserted through the pin hole 60 and served to physically align the insert 18 onto the die shaft 14. Once the insert is aligned and held in position by the pin, the machine bolts can be inserted into the apertures 56 and be threaded into threaded bores formed in the die shaft 14. It should be noted that the pin hole 60 is an optional feature and is present only for convenience in mounting the insert 18 onto the die shaft 14.

A particular attachment mechanism for attaching a replaceable and/or interchangeable die cutting insert 18 onto the outer circumference 16 of the die shaft 14 is described in pending provisional patent application entitled "A DIE CUTTING INSERT FOR A ROTARY DIE CUTTER AND THE DIE ITSELF," filed Jan. 26, 1996 and having U.S. Ser. No. 60/010,636 and which has now been converted into a regular patent application having the same title filed Jun. 21, 1996 and having U.S. Ser. No. 08/667,578. The teachings of this patent application are incorporated by reference and made a part hereof.

Figure 4:
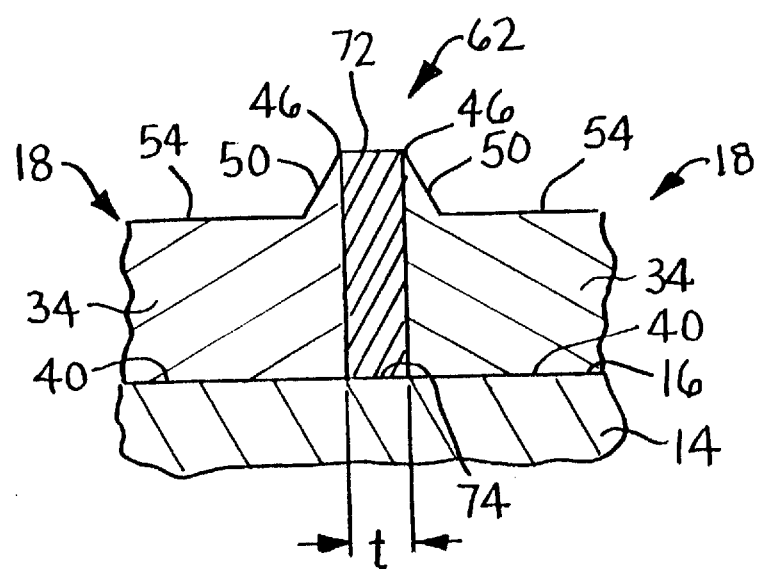
FIG. 4 is an exploded cross-sectional view taken along line 4—4 of FIG. 3 depicting the cutting edges of a pair of adjacent die cutting inserts with a compressible material sandwiched therebetween when mounted on a die shaft.

Referring to FIGS. 3 and 4, the knife shaft assembly 13 includes means 62 for preventing the build-up of cut waste material between adjacent die cutting inserts 18. The means 62 is a compressible material such as natural or synthetic rubber, or some other type of material having compressible characteristics. When cutting absorbent articles 24, such as sanitary napkins and pantiliners, it is necessary that the compressible material 62 be approved by the U.S. Food and Drug Administration (FDA). A material which is FDA approved is neoprene rubber, model #8616K24 which is commercially available from McMaster-Carr Supply Company, PO Box 4355, Chicago, Ill., 60680-4355. This particular neoprene rubber comes in sheet form and can be cut or stamped into any desired shape. The neoprene rubber should have a tensile strength of between about 100 pounds per square inch (psi) to 2,000 psi, preferably between about 500 psi to about 1,500 psi, and most preferably, between about 1,000 to about 12,000 psi. This particular material is off-white in color having a durometer hardness classified as Shore "A." The neoprene has an operable temperature range of between about −25° F. to about 220° F. Neoprene is a synthetic rubber produced by polymerization of chloroprene and used in weather-resistant products, adhesives, shoe soles, paints and rocket fuels. The compressible material 62 can have a thickness which can vary from between about 0.001 inches to about 0.5 inches. Preferably, the compressible material 62 has a thickness of between about 0.01 inches to about 0.25 inches, and most preferably, has a thickness of between about 0.01 inches to about 0.1 inches. For most applications, the use of a compressible material 62 having a thickness of less than about 0.25 inches will suffice.

As shown in FIG. 3, the die cutting inserts 18 are arranged in an end-to-end configuration about the outer circumference 16 of the die shaft 14. The inserts 18 can be arranged in a spaced apart configuration having an opening of from between about 0.001 inches to about 0.5 inches between each adjacent insert. In FIG. 3, one will also notice that the inserts 18 are arranged in a side by side, offset configuration across the width "w" of the die shaft 14. Preferably, there will be at least one roll of inserts arranged about the outer circumference 16 of the die shaft 14. More preferably, for increased efficiency, it is advantageous to arrange the die cutting inserts 18 across the entire width "w" of the die shaft 14 so as to be able to cut a greater number of articles 24 for each revolution of the die shaft 14. In FIG. 3, four die cutting inserts 18 are shown arranged in an offset pattern across a major portion of the width "w" of the die shaft 14. It should be noted that the particular configuration of the die cutting inserts 18 will dictate as to how each of the inserts 18 can be nested so as to produce the most cuts while obtaining the least amount of cut waste material. It has been found that the use of two to twelve, side by side rolls across the width "w" of the die cutter 18, works well. The number of inserts 18 aligned end to end around the outer circumference 16 of the die shaft 14 will be dependent upon the length of each insert and the diameter of the die shaft 14. It should be noted that all of the inserts 18 do not have to be identical in size or dimension. For example, two or more different articles can be produced by mounting different shaped inserts 18 on the die shaft 14.

In FIG. 3, the compressible means 62 is shown in a grid-like arrangement having one or more ring or band members 64 of compressible material extending circumferentially about the outside circumference 16 of the die shaft 14. The ring or band members 64 can be continuous about the 360° circumference or they can be arcuate segments which are assembled so as to form a complete circle or a portion of a complete circle. The grid work also includes one or more transverse member 66 positioned between the ends of each pair of adjacent inserts 18. The ring members 64 and the transverse member 66 can have a thickness "t" as labeled in FIG. 4, of between about 0.001 inches to about 0.5 inches. Preferably, the thickness is less than 0.025 inches, and most preferably, the thickness is between about 0.01 inches to about 0.1 inches. If one has the opportunity to size the diameter of the die shaft 14 so as to maximize the number of inserts 18 which can be mounted onto the outer circumference 16 thereof, one can reduce the distance between the ends of adjacent inserts 18. By reducing the distance therebetween, one can minimize the amount of cut waste material in the manufacturing process. This is a very advantageous feature. For this reason, it is preferable to dimension the end-to-end clearance distance to range between about 0.01 to about 0.05 inches, if possible.

It is likewise important to minimize the clearance distance between two adjacent side-by-side inserts 18. However, the outer configurations of the inserts 18 may require that the clearance be larger than that between the end-to-end arrangement. It is anticipated that the ring or band members 64 may have a thickness which is slightly larger than the thickness of the transverse member 66. By slightly larger, it is meant that the thickness may be in the range of between 0.001 inches to about 0.1 inches, and preferably, will be about 0.05 inches. It should also be noted that the ring members 64 and the transverse member 66 do not have to be physically bonded or attached together but can be merely held in position by the physical arrangement of the inserts 18. One will notice that in FIG. 3, a first flange 68 is secured to the left-hand side of the die shaft 14 and a second flange 70 is attached to the right-hand side of the die shaft 14. The flanges 68 and 70 are configured to conform to the outer profile of the circumferential row of inserts 18 and assist in sandwiching the ring member 64 against the cutting edges 46 of the aligned inserts 18. Located between each circumferential row of inserts 18, is the compressible material 62. The compressible material 62 will be sandwiched between each pair of cutting edges 46 by the physical engagement with the inserts 18. It should be noted that in assembling the compressible material 62, it is anticipated that the compressible material 62 will be squeezed to a certain extent in the assembly process. The amount that the compressible material 62 is squeezed will be dependent upon one's manufacturing process and the type of tooling used.

FIG. 4 shows an embodiment wherein the compressible material 62 is positioned between two adjacent inserts 18. The compressible material 62 contains a top surface 72 which is aligned approximately flush with a horizontal plane aligned tangential to the tips of the cutting edges 46. It should be noted that the top surface 72 can be positioned slightly below the plane of the cutting edges 46 but should not be at a distance below the plane which is greater than the thickness of the web of material 22 which is being cut. For example, if the web is about 0.125 inches thick, the top surface 72 of the compressible material 62 should not be below the plane by more than about 0.1 inches or the benefit of utilizing the compressible material 62 will be lost. Preferably, the compressible material 62 is equal to or slightly below the plane created by the adjacent cutting edges 46. It is possible to have the compressible material 62 extend above the plane of the cutting edges 46 but in this position, the compressible material may interfere with the ability of the cutting edges 46 to properly cut the web of material cleanly. A very slight extension, in the range of between about 0.0001 to about 0.1, above the plane of the adjacent cutting edges 46 should be acceptable. It should also be noted that if a compressible material 62 is used which has a soft or medium compressibility value, a value which allows the material to be easily compressed, that a greater distance above the plane of the cutting edges 46 could possibly be used. For a compressible material having a firm or hard compressibility value, it is recommended that the top surface 72 of the compressible material 62 does not extend above the plane of the cutting edges 46.

The compressible material 62 also includes a bottom surface 74 which can be flush with the bottom surface 40 of each of the inserts 18. As shown in FIG. 4, when the bottom surface 74 is flush with the bottom surface 40 of the inserts 18, all of the surfaces will mate with the outer circumference 16 of the die shaft 14. This will assure that as the compressible material 62 is compressed from above, by contacting the material web 22, that it will not be pushed down to a permanent lower position which is below the plane of the cutting edges 46. The purpose of the compressible material 62 is to compress down below the cutting edges 46 as the material web 22 is being cut and then to extend back to its normal position expelling any potential fibers or waste material which may be present. The waste material located between the adjacent cutting edges 46 can then be removed as the knife shaft assembly 13 rotates about its center axis. The compressible material 62 should be selected to have a particular tensile strength and compressibility value. These values can vary depending upon the type of material selected, the thickness of the material, the type of material being cut, as well as other factors. A compressible material is normally classified as being a "soft, medium, firm or hard" grade. For this invention, the compressible material 62 should be selected to be either "soft, medium or firm" grade but not "hard" grade. The "soft grade 35–45 A" and the "medium grade 45–55 A" seems to work best when using the compressible material 62 between adjacent cutting edges 46 for cutting absorbent articles, such as sanitary napkins and pantiliners. The "firm grade 55–65 A" might work better for a harder material which is to be cut. It is anticipated that the compressibility values of the material 62 will range from between about 0.1× to about 10×, preferably between about 0.1× to about 5×, and most preferably, the compressibility value is less than about 3×. By 1×, it is meant that the compressible material 62 can be compressed to half of it's thickness. The tensile strength of the material 62 can also vary and should range between about 450 psi to about 1,500 psi, more preferably between about 750 to about 1,500, and most preferably, between about 1,000 psi to about 1,300 psi.

It should be noted that the compressible material 62 can be positioned about at least a portion of the periphery of the first surface 40 of each of the adjacent inserts 18. The top surface 72 of the compressible material 62 can be curved or arcuate in shape so as to match the profile of the cutting edge 46 of the knives 44. It should also be noted that if the cutting edges 46 are flat or linear, then the top surface 72 of the compressible material 62 can also be flat or linear. The compressible material 62 can be positioned about the outer circumference of each of the inserts 18 but does not have to be in physical contact with the entire outer circumference of each of the inserts 18. For example, if one looks at FIG. 3, one will notice that the compressible material 62 actually forms an approximately rectangular grid work around the hourglass shape inserts 18. Physical contact about the entire periphery of the insert 18 does not occur.

It should also be noted that it is possible for one to form a particular grid-like arrangement of the compressible materials 62 and then to place it, like a template, over the outer circumference 16 of the die shaft 14. Once the grid work of the compressible material 62 is in place, each of the individual inserts 18 can then be bolted onto the die shaft 14. This and other particular configurations will be obvious to those skilled in the art and are considered part of the present invention.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

I claim:

1. A knife shaft assembly comprising:

a) a rotatable die shaft having an outer circumference and having a defined width;

b) at least two die cutting inserts mounted on said outer circumference of said die shaft, each of said die cutting inserts having a first surface and a knife formed about the periphery of said first surface, said knife having a cutting edge and a sidewall aligned at an angle of between 20° to about 50° relative to said cutting edge, and each die cutting insert being adjacently aligned to another die cutting insert and having a portion of said respective cutting edge spaced within 0.5 inches of a portion of said cutting edge of said adjacently aligned die cutting insert; and c) grid work means for preventing buildup of material waste between said adjacently aligned die cutting inserts, said grid work means comprising a grid work of continuous compressible band members and transverse members positioned completely exterior to the peripheries of said die cutting inserts and forming a substantially rectangular grid work band outside of each one of said die cutting insert peripheries, said compressible band members not extending laterally beyond an adjacent one of said die cutting inserts more than about 0.1 inches and said compressible band members having a thickness of between about 0.01 inches to about 0.5 inches.

2. The knife shaft assembly of claim 1 wherein said die cutting inserts are arranged in an end to end configuration around said outer circumference of said die shaft.

3. The knife shaft assembly of claim 1 wherein said die cutting inserts are arranged to form at least two rows of cutters about the periphery of said outer circumference.

4. The knife shaft assembly of claim 3 wherein said die cutting inserts are arranged in a side by side configuration.

5. The knife shaft assembly of claim 3 wherein said die cutting inserts are arranged in an offset, side by side configuration.

6. The knife shaft assembly of claim 1 wherein said compressible band members are made of neoprene rubber.

7. The knife shaft assembly of claim 6 wherein said neoprene rubber has a tensile strength of at least 1,000 psi.

8. A knife shaft assembly comprising:
a) a rotatable die shaft having an outer circumference and having a defined width;
b) a plurality of die cutting inserts mounted on said outer circumference of said die shaft, each of said die cutting inserts having a first surface and a knife integrally formed about the periphery of said first surface, said knife having a cutting edge and a sidewall aligned at an angle of between about 25° to about 50° relative to said cutting edge, and each of said die cutting inserts being adjacently aligned to another die cutting insert and arranged to form at least one row of cutters around said outer circumference of said die shaft; and
c) grid work means for preventing buildup of material waste between said adjacently aligned die cutting inserts, said grid work means comprising a grid work of continuous compressible band members and transverse members positioned completely exterior to the peripheries of said die cutting inserts and forming a substantially rectangular grid work band outside of each one of said die cutting insert peripheries, said compressible band members not extending laterally beyond an adjacent one of said die cutting inserts more than about 0.1 inches and said compressible band members having a thickness of between about 0.01 inches to about 0.5 inches.

9. The knife shaft assembly of claim 8 wherein said compressible band members have an upper surface which is aligned approximately flush with said knives.

10. The knife shaft assembly of claim 8 wherein said compressible band members are made of neoprene rubber.

11. The knife shaft assembly of claim 8 wherein said compressible band members have a thickness of between about 0.01 inches to about 0.25 inches.

12. A knife shaft assembly comprising:
a) a cylindrically shaped die shaft having an outer circumference and having a defined width;
b) a plurality of replaceable die cutting inserts mounted on said outer circumference of said die shaft, each of said die cutting inserts having first and second spaced apart ends, first and second oppositely aligned surfaces, and a knife integrally formed about the periphery of said first surface, said knife having a cutting edge and a sidewall aligned at an angle of between about 25° to about 50° relative to said cutting edge, each of said die cutting inserts being adjacently aligned to another die cutting insert and having a portion of said respective cutting edge spaced within 0.5 inches of a portion of said cutting edge of said adjacently aligned die cutting insert, and said die cutting inserts being arranged in an end to end configuration around said outer circumference of said die shaft and in an offset, side by side arrangement across at least a portion of said defined width of said die shaft; and
(c) grid work means for preventing buildup of material waste between said adjacently aligned die cutting inserts, said grid work means comprising a grid work of continuous compressible band members and transverse members positioned completely exterior to the peripheries of said die cutting inserts and forming a substantially rectangular grid work band outside of each one of said die cutting insert peripheries, said compressible band members not extending laterally beyond an adjacent one of said die cutting inserts more than about 0.5 inches and said compressible band members having a thickness of between about 0.01 inches to about 0.5 inches.

13. The knife shaft assembly of claim 12 wherein said compressible band members are made of natural rubber.

14. The knife shaft assembly of claim 12 wherein said compressible band members have a thickness of between about 0.001 inches to about 0.5 inches.

15. The knife shaft assembly of claim 14 wherein said compressible band members have a thickness of between about 0.05 inches to about 0.25 inches.

16. The knife shaft assembly of claim 14 wherein said compressible band members have a thickness of between about 0.1 inches to about 0.2 inches.

17. The knife shaft assembly of claim 12 wherein said compressible band members have an upper surface which is aligned approximately flush with said knives.

18. A knife shaft assembly comprising:
a) a rotatable die shaft having an outer circumference and having a defined width;
b) a plurality of replaceable die cutting inserts mounted on said outer circumference of said die shaft, each of said die cutting inserts having a first surface and a continuous knife integrally formed about the periphery of said first surface, said continuous knife having a cutting edge and a sidewall aligned at an angle of between about 25° to about 50° relative to said cutting edge, and each of said die cutting inserts being adjacently aligned to another die cutting insert and arranged to form at least two rows of cutters around said outer circumference of said die shaft and which extend across at least a portion of said defined width; and
c) grid work means for preventing buildup of material waste between at least some of said adjacently aligned die cutting inserts, said grid work means comprising a grid work of continuous compressible band members and transverse members positioned completely exterior to the peripheries of said die cutting inserts and forming a substantially rectangular grid work band outside of each one of said die cutting insert peripheries, said compressible band members not extending laterally beyond an adjacent one of said die cutting inserts more than about 0.1 inches and said compressible band members formed from a sheet of soft grade Neoprene rubber having a tensile strength of 500 psi to 1500 psi, a compressibility value less than about 3×, and a thickness of between about 0.01 inches to about 0.5 inches.

19. The knife shaft assembly of claim 18 wherein there are at least four rows of said die cutting inserts arranged across said defined width of said die shaft.

20. The knife shaft assembly of claim 18 wherein each of said inserts has a central longitudinal axis and said inserts are arranged about said outer circumference of said die shaft such that each of said longitudinal axes extend around at least a portion of said outer circumference.

* * * * *